(12) United States Patent
Kristian et al.

(10) Patent No.: US 7,348,135 B2
(45) Date of Patent: Mar. 25, 2008

(54) ASSAY FOR DETECTING CHANGES IN MITOCHONDRIAL MEMBRANE PERMEABILITY AND METHOD OF USING SAME

(75) Inventors: Tibor Kristian, Severna Park, MD (US); Gary Fiskum, Upper Falls, MD (US)

(73) Assignee: University of Maryland, Baltimore, MD (US)

( * ) Notice: Subject to any disclaimer, the term of this patent is extended or adjusted under 35 U.S.C. 154(b) by 395 days.

(21) Appl. No.: 10/925,913

(22) Filed: Aug. 26, 2004

(65) Prior Publication Data
US 2005/0048596 A1    Mar. 3, 2005

Related U.S. Application Data

(60) Provisional application No. 60/498,719, filed on Aug. 28, 2003.

(51) Int. Cl.
*C12Q 1/00* (2006.01)

(52) U.S. Cl. .............................. 435/4; 435/25; 435/26; 435/28; 435/317.5

(58) Field of Classification Search ................... None
See application file for complete search history.

(56) References Cited

OTHER PUBLICATIONS

Kristian, Tibor, et al.; "A Fluorescence-Based Technique for Screening Compounds That Protect Against Damage to Brain Mitochondria"; Brain Research Protocols, vol. 13, pp. 176-182, 2004.

*Primary Examiner*—Leon B Lankford, Jr.
*Assistant Examiner*—Allison M. Ford
(74) *Attorney, Agent, or Firm*—Gilberto M. Villacorta; Victoria S. Rutherford; Foley & Lardner LLP

(57) ABSTRACT

An assay for assessing the permeability of mitochondrial membranes is provided. The assay is based on enzymatic reactions that produce a detectable signal in the presence of intra-mitochondrial compounds. In some embodiments, the intra-mitochondrial compounds may be reduced and/or oxidized nicotinamide adenine dinucleotides (i.e., NADH and $NAD^+$, respectively). The assay may optionally be provided in the form of a kit, and may further be useful in the discovery and interrogation of compounds that may serve to inhibit pathologic increase in mitochondrial membrane permeability, which is associated with numerous and varied mammalian disease.

8 Claims, 6 Drawing Sheets

ASSAY FOR DETECTING CHANGES IN MITOCHONDRIAL MEMBRANE PERMEABILITY AND METHOD OF USING SAME

FIELD OF THE INVENTION

The present invention relates generally to pathology and diagnostic biological assays. More specifically, the present invention relates to an enzymatic assay for the detection of changes in mitochondrial membrane permeability.

BACKGROUND OF THE INVENTION

Mitochondria play a key role in generating ATP for energy-dependent processes in cells. Therefore, mitochondrial dysfunctions often have significant effect on cell function and survival. For example, when mitochondrial membranes are damaged, mitochondria lose their membrane potential, uncoupling oxidative phophorylation and preventing ATP production therefrom, and intra-mitochondrial solutes are released, some of which induce cell death.

One of the better-characterized mechanisms leading to pathologic increase in permeability of mitochondrial membranes is the opening of the mitochondrial permeability transition (MPT) pore. This is a high-conductance, nonspecific channel in the intra-mitochondrial membrane that conducts solutes up to 1.5 kDa. The pore opening is regulated by multiple effectors and therefore, its opening is not readily predicted.

When open, however, MPT pores lead to osmotic swelling of mitochondria, which can cause irreversible damage to their membranes. Several techniques have been proposed for assessing the induction of MPT in mitochondria by detecting the pathologic increase in their membrane permeability. These techniques are based on monitoring the translocation of a specific marker through damaged mitochondrial membranes. Thus, either mitochondria are incubated in the presence of a fluorescent or radioactive marker which is taken up only by injured mitochondria, or the mitochondria are preloaded with markers that are released upon a significant increase in mitochondrial membrane permeability.

These techniques, however, have several disadvantages and are not suitable, for example, in drug screening applications. Notably, both techniques require manipulations with mitochondria before the actual marker translocation is assessed. Furthermore, several control experiments are required to exclude possible respiratory inhibition, calcium uptake blocking, or uncoupling of mitochondria. Usually background signals are high, therefore significantly limiting the sensitivity of the detection assay.

SUMMARY OF THE INVENTION

The foregoing needs are met, to an extent, by the present invention, in which in one embodiment, a method of assessing the integrity of a mitochondrial membrane is provided, comprising: (a) contacting a sample comprising isolated mitochondria with a mixture of enzymes, which mixture catalyzes at least two coupled, cyclic enzymatic reactions that utilize an intra-mitochondrial substance, if present in the sample, as a substrate in at least one of said coupled, cyclic enzymatic reactions and in which at least the other of said coupled, cyclic enzymatic reactions generates a detectable signal; and (b) correlating said detectable signal, if generated, to the presence of said intra-mitochondrial substance, thereby implicating a breach in said mitochondrial membrane. The intra-mitochondrial compound may be a pyridine nucleotide, preferably $NAD^+$ or NADH. Further, the isolated mitochondria may be isolated from liver. The mixture of enzymes may comprise alcohol dehydrogenase (ADH), NADH oxidase (Ox), horseradish peroxidase (HRP), or a combination thereof; and, the detectable signal may be a luminescent product, a fluorescent product, or a spectrophotometrically detectable product.

In another embodiment of the present invention, a method of assessing the integrity of a mitochondrial membrane is provided, comprising: (a) contacting a sample comprising isolated mitochondria with a mixture of enzymes, which mixture catalyzes at least one cyclic enzymatic reaction that utilizes an intra-mitochondrial compound as a substrate, if present in the sample, and in so doing generates a byproduct; and (b) detecting and correlating the byproduct, if generated, to the presence of the intra-mitochondrial compound, thereby implicating a breach in said mitochondrial membrane. The intra-mitochondrial compound may be a pyridine nucleotide, and preferably $NAD^+$ or NADH in some embodiments. The isolated mitochondria can be isolated from liver. In some embodiments, the mixture of enzymes comprise ADH, NADH oxidase, HRP, or a combination thereof, and the byproduct is $H_2O_2$.

In yet another embodiment of the present invention, a method of assessing the integrity of a mitochondrial membrane is provided, comprising: (a) subjecting a sample comprising isolated mitochondria and a suitable buffer to a first cyclic enzymatic reaction, which cyclic reaction produces a reduced first substrate from a first substrate, which is an intra-mitochondrial compound; (b) subjecting the sample to a second cyclic enzymatic reaction, which second cyclic reaction oxidizes the reduced first substrate while also giving rise to a reduced second substrate and producing a detectable signal; (c) measuring the signal and correlating the integrity of the mitochondrial membrane therefrom. The intra-mitochondrial compound may be a pyridine nucleotide, preferably $NAD^+$ or NADH in some embodiments. The mitochondria may also be isolated from liver. In some embodiments, the detectable signal is selected from the group consisting of a luminescent product, a fluorescent product, and a spectrophotometrically detectable product. The method may comprise at least one enzymatic reaction that uses ADH, NADH oxidase, HRP. In some embodiments, the first cyclic enzymatic reaction comprises ADH and NADH Ox, the second cyclic enzymatic reaction comprises NADH Ox and HRP, and/or the enzymatic reaction of (b) is fluorescent. The enzymatic reaction may also include HRP, optionally in converting Amplex Red to Resorufin. The detectable signal may also be produced by accumulation of NADH, reduction of $NAD^+$ and/or an accumulation of $H_2O_2$.

In still another embodiment of the present invention, a method for detecting intra-mitochondrial pyridine nucleotides in a biological sample of isolated mitochondria is provided comprising (a) subjecting the biological sample comprising isolated mitochondria and a suitable buffer to a first enzyme which reduces any pyridine nucleotide, generating a reduced pyridine nucleotide; (b) subjecting the biological sample to a second enzyme which oxidizes the reduced pyridine nucleotide thereby producing a reduced substrate; (c) subjecting at least a portion of the sample of (c) with a third enzyme which oxidizes the reduced substrate to produce a detectable signal; and (d) determining the concentration of pyridine nucleotide present in the buffer of the biological sample by correlating the detectable signal. The intra-mitochondrial pyridine nucleotide may be $NAD^+$ or NADH. In some embodiments, the first enzymatic reaction uses an alcohol dehydrogenase, preferably ADH, to generate the pyridine nucleotide. In other embodiments, the second enzyme is NADH Ox and/or the third enzyme is HRP. The reduced substrate may be $H_2O_2$, and preferably the third enzymatic reaction uses HRP to oxidize the $H_2O_2$. The method may further comprise using a portion of the patient sample not reacted with the first enzyme in the third enzymatic reaction to establish a background level of substrates detected in the third enzymatic reaction.

In still yet another embodiment of the present invention, a diagnostic kit for the assessment of permeability of mitochondrial membranes is provided comprising: (a) a first enzyme that oxidizes an alcohol to an aldehyde thereby reducing an intra-mitochondrial compound; and (b) a second enzyme that oxidizes the intra-mitochondrial compound giving rise to a reduced first substrate; and (c) a third enzyme that oxidizes the reduced first substrate producing a detectable signal from a second substrate. The first enzyme may be an alcohol dehydrogenase and the alcohol ethanol. Also, the second enzyme may be NADH oxidase. In some embodiments, the intra-mitochondrial compound is a pyridine nucleotide, preferably NADH or $NAD^+$. The third enzyme may be HRP and the second substrate Amplex red. The detectable signal may be a chromophore or a fluorophore, optionally Resorufin. The diagnostic kit of claim may further comprise a package and instructions.

In further still yet another embodiment of the present invention, a method for identifying compounds of interest which reduce or prevent the migration of an intra-mitochondrial compound in response to a mitochondria damaging agent is provided comprising: (a) exposing a sample comprising isolated mitochondria and a suitable buffer to a test compound; (b) exposing the sample of (a) with the mitochondria damaging agent under conditions and for a time sufficient to allow migration of the intra-mitochondrial compound into the buffer; (c) measuring a detectable signal resulting from the interaction of the intra-mitochondrial compound and one or a series of enzymatic reactions, which reactions produces a detectable signal; (d) comparing, if any, the increase or decrease in the detectable signal relative to the absence of the test compound. The mitochondria damaging agent may be cyclosporin A (CsA) or Bongkrekic acid (BA), and the detectable signal may be selected from the group consisting of a luminescent product, a fluorescent product, and a spectrophotometrically detectable product. Furthermore, at least one enzymatic reaction may use ADH, NADH oxidase, HRP.

In further still yet another embodiment of the present invention, A method to detect a disease condition in a subject comprising: (a) subjecting a biological sample comprising mitochondria isolated from an organ of the subject and a suitable buffer to a first enzyme which reduces an oxidized pyridine nucleotide, generating a reduced pyridine nucleotide; (b) subjecting the biological sample to a second enzyme which oxidizes the reduced pyridine nucleotide giving rise to a reduced substrate; (c) subjecting the biological sample to a third enzyme which oxidizes the reduced substrate to produce a detectable signal; (d) determining the permeability of the mitochondrial membranes of the subject by measuring the detectable signal; and (e) correlating the permeability of the mitochondrial membrane to the disease condition by comparison to a permeability of mitochondrial membranes from control subjects. The disease may be characterized by one of ischemia, hypoxia, anoxia, hypoglycemic coma, seizures, stroke, physical trauma, myocardial infarction, drug toxicity, chemical toxicity, Alzheimer's disease, Parkinson's disease, or Huntington disease. The detectable signal may be selected from the group consisting of a luminescent product, a fluorescent product, and a spectrophotometrically detectable product, and at least one enzymatic reaction may use ADH, NADH oxidase, HRP in some embodiments.

In further still yet another embodiment of the present invention, a method for assessing the permeability of mitochondrial membranes to intra-mitochondrial pyridine nucleotides is provided comprising: (a) exposing a cell having a cell membrane and in a suitable buffer to a permeabilizing agent to permeabilize the cell membrane; (b) washing the cells to remove the suitable buffer from (a); (c) replacing the suitable buffer; (d) exposing the cells from (c) with a mitochondrial membrane damaging agent; (e) subjecting the cells from (d) with a first enzyme which reduces the pyridine nucleotide, generating a reduced pyridine nucleotide; (f) subjecting the cells from (d) to a second enzyme which oxidizes the reduced pyridine nucleotide thereby producing a reduced substrate; (g) subjecting the cells from (d) to a third enzyme which oxidizes the reduced substrate to produce a detectable signal; and (h) determining the concentration of pyridine nucleotide by measuring the detectable signal. The permeabilizing agent may be digitonin or a saponin.

In further still yet another embodiment of the present invention, a method for identifying compounds of interest which reduce or prevent the migration of an intra-mitochondrial compound in response to a mitochondria damaging agent is provided comprising: (a) contacting a cell having a cell membrane and in a suitable buffer with a permeabilizing agent to permeabilize the cell membrane; (b) washing the cells to remove the suitable buffer from (a); (c) resuspending the washed cells from (b) with the suitable buffer; (d) exposing the cells from (c) to a test compound; (e) exposing the sample of (d) with the mitochondria damaging agent under conditions and for a time sufficient to allow migration of the intra-mitochondrial compound into the buffer; (f) measuring a detectable signal resulting from the interaction of the intra-mitochondrial compound and one or a series of enzymatic reactions, which reactions produces a detectable signal; (d) comparing, if any, the increase or decrease in the detectable signal relative to the absence of the test compound.

There has thus been outlined, rather broadly, certain embodiments of the invention in order that the detailed description thereof herein may be better understood, and in order that the present contribution to the art may be better appreciated. There are, of course, additional embodiments of the invention that may be described below and which may form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art may appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

In accordance with one embodiment of the present invention, an assay is provided to assess changes in permeability of mitochondrial membranes to intra-mitochondrial solutes. The permeability of mitochondrial membranes, in many instances, can be correlated with the "integrity" of the membranes. By "integrity," it is meant the ability of mitochondrial membranes to retain solutes and molecules that are generally sequestered within the confines of mitochondrial membranes of healthy, functional mitochondria. In the event a mitochondrial membrane is "breached," solutes and molecules that are normally retained within the mitochondria permeate the bounds of the mitochondrial membranes into the cytosol of whole cells, or buffer, in isolated mitochondria.

The present invention provides a relatively straight-forward, sensitive assay that is capable of detecting damage to mitochondrial membranes without the need to preload the organelles with a specific marker or other manipulations. Instead, the present assay employs a combination of enzymatic reactions which, in concert, is able to detect the migration of endogenous intra-mitochondrial solutes out of membrane-damaged mitochondria.

Intra-mitochondrial solutes include, by way of example, pyridine nucleotides (e.g., $NAD^+$, NADH, NADPH, NADPH) and/or proteins (e.g., citrate synthase, pyruvate dehydrogenase). Any known solute that is thought to ordinarily reside within the outer membrane of healthy mitochondria may be used in accordance with the teachings herein. Detectable signals include, luminescent products, fluorescent products, chromophores, and/or any spectrophotometrically detectable product. A preferable fluorescent compound is the highly fluorescent molecule, Resorufin. By way of example, chromophores include, but are not limited to, GFP and its mutants or luciferase and its mutants. A variety of methods and agents can be used to induce mitochondrial membrane damage, including calcium.

By way of example, pyridine nucleotides (PNs) may be easily adapted for enzymatic detection. PNs from mitochondria cannot pass the membranes under normal physiological conditions, and therefore, increase in extra-mitochondrial PN levels is thought to be reflective of loss of mitochondrial membrane integrity.

Figure 1:
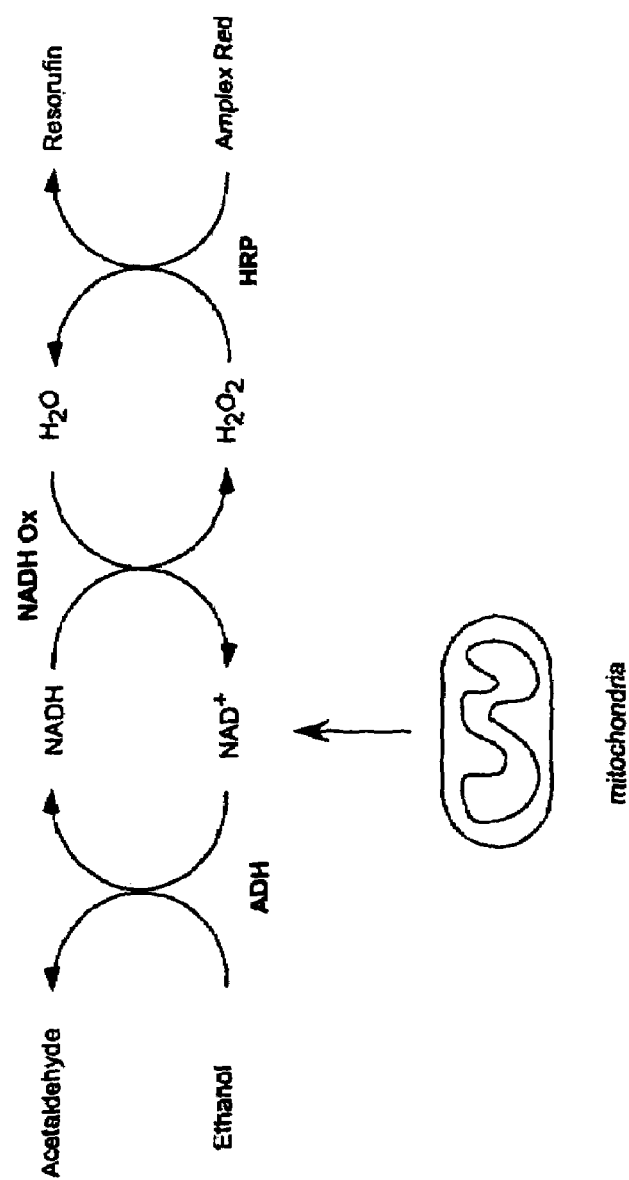
FIG. 1 shows a schematic diagram of an enzymatic reaction of one assay in accordance with an embodiment of the present invention.
Figure 2:
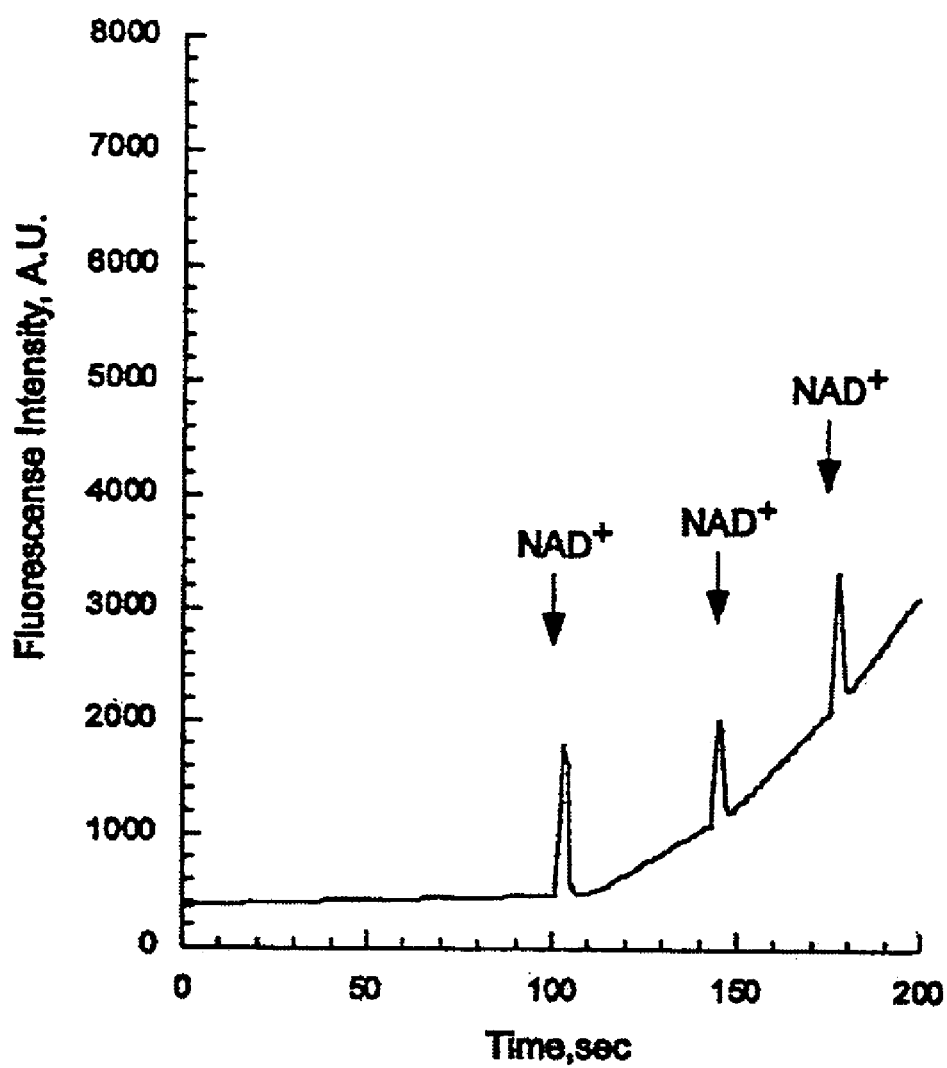
FIG. 2 is graph depicting changes in fluorescent intensity due to Resorufin production in the assay mixture following indicated $NAD^+$ additions (25 nmol each).
Figure 3:
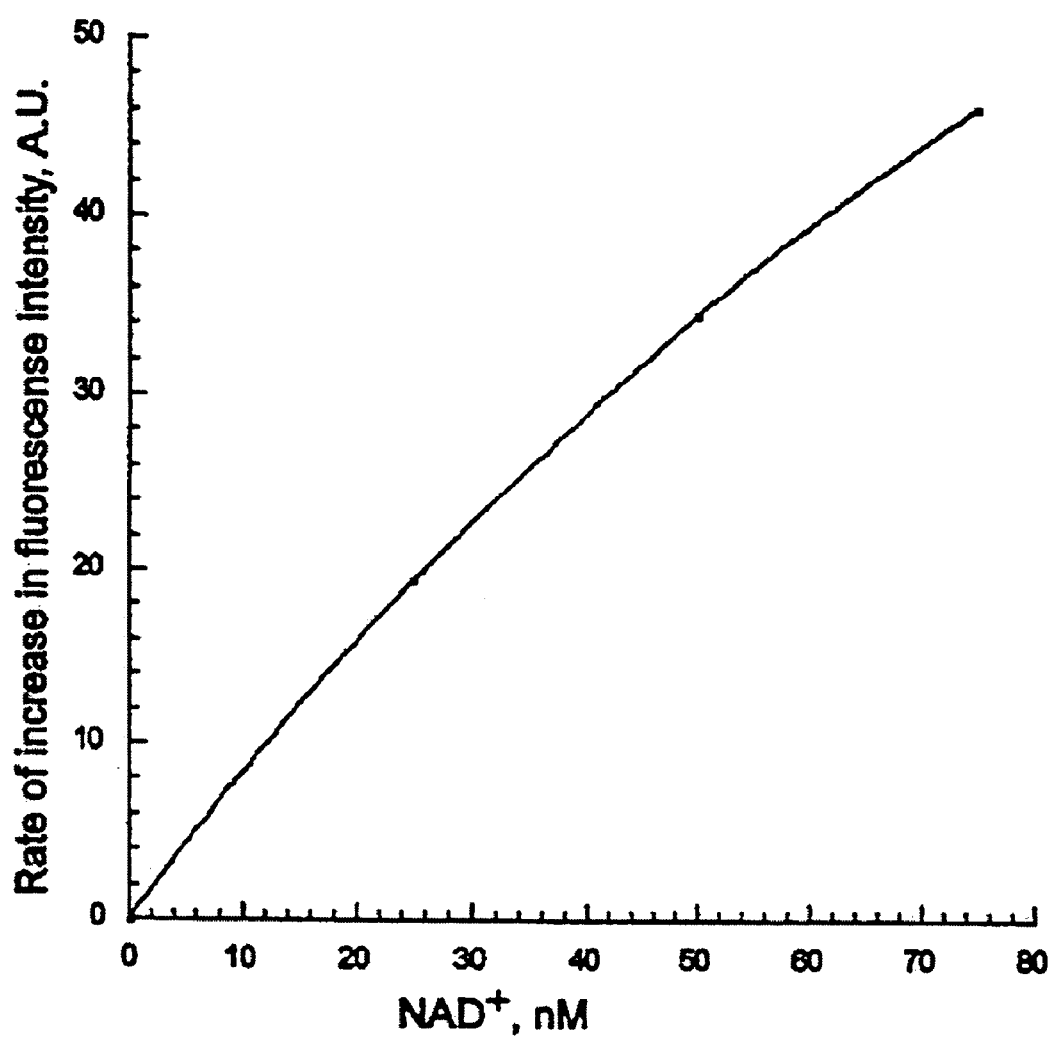
FIG. 3 is a graph illustrating the relationship between fluorescence and concentration of $NAD^+$. Measurements were recorded at 25 nmol intervals.
Figure 4:
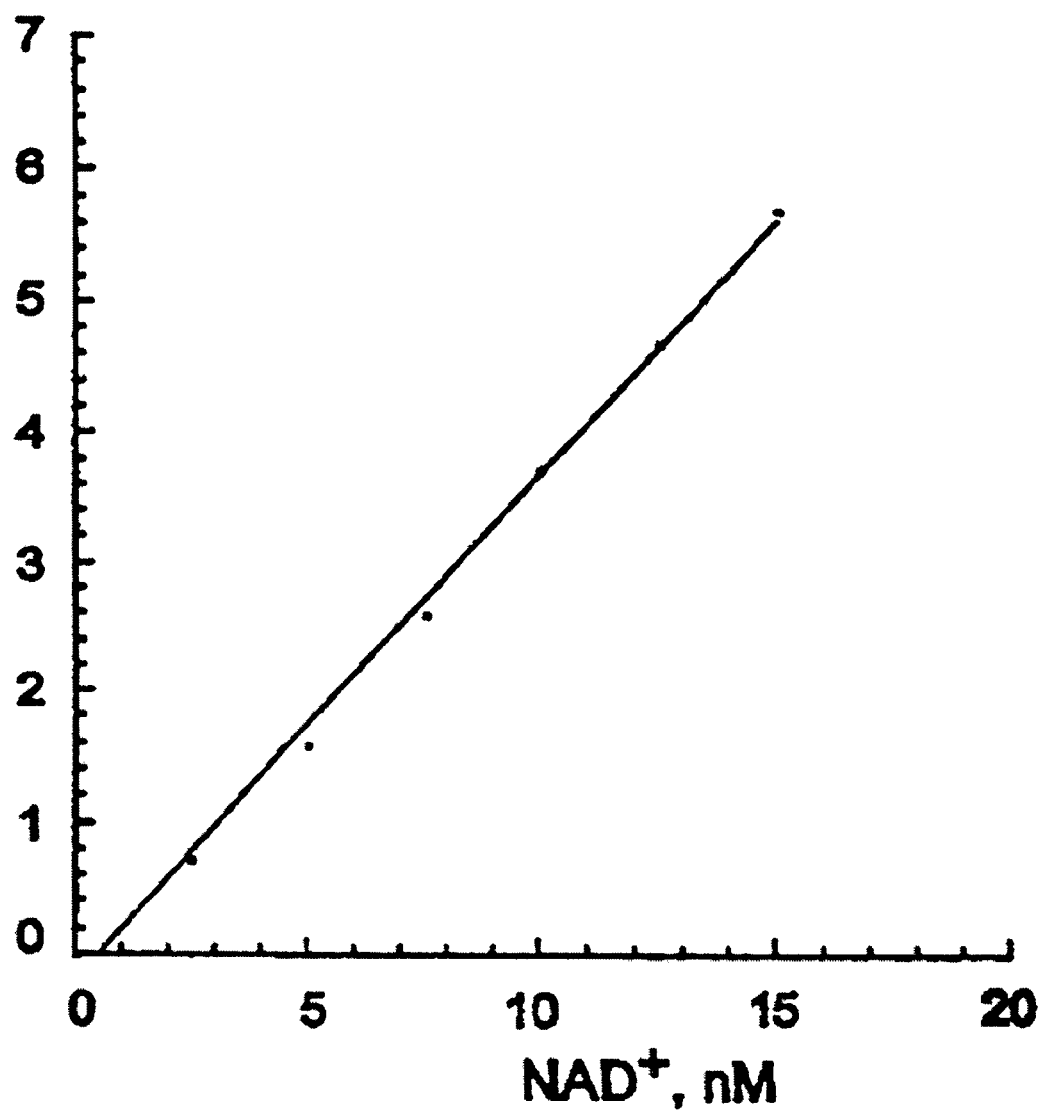
FIG. 4 is a graph illustrating the relationship between fluorescence and concentration of $NAD^+$ at nanomolar levels. Measurements were recorded at 2.5 nmol intervals.

In one preferred embodiment, the assay for pyridine nucleotides measurement may comprise several enzymatic reactions—cyclic and/or coupled—which use oxidized or reduced form of nicotinamide adenine dinucleotides ($NAD^+$, NADH, respectively) as substrate, thereby providing a detectable final product (FIG. 1). In the first step shown in FIG. 1, alcohol dehydrogenase (ADH) converts ethanol to acetaldehyde in the presence of $NAD^+$, which is released from mitochondria and reduced to NADH. In the next reaction NADH oxidase (Ox) oxidizes NADH back to $NAD^+$, and hydrogen peroxide ($H_2O_2$) is produced from water in the process. In the last reaction, horseradish peroxidase (HRP) produces a detectable signal in the presence of hydrogen peroxide. In the example illustrated, Amplex red is converted into Resorufin.

A "cyclic" enzymatic reaction is defined herein as one that involves at least two enzymatic reactions, in which the substrate and product of one reaction are the product and substrate of another, respectively. For example, in FIG. 1, NADH Ox and ADH comprise a cyclic enzymatic reaction, wherein substrate (NADH) and product ($NAD^+$) of the NADH Ox reaction are conversely the product (NADH) and substrate ($NAD^+$) of the ADH reaction. Reactions are herein said to be "coupled" in cases where the product of one reaction is used subsequently in a another reaction. For example, NADH Ox and HRP comprise a coupled enzymatic reaction in that one product of the NADH Ox reaction, $H_2O_2$, is subsequently used by HRP as a substrate. For clarity, cyclic reactions may also be coupled reactions. As well, two cyclic enzymatic reactions that share a common product/substrate may be defined as coupled cyclic enzymatic reactions.

A variety of buffering systems are known to one of ordinary skill in the art and may be used in the present invention. Preferably, the buffers are capable of maintaining the integrity of the mitochondrial membranes in the absence of damaging agents to same. Alternatively, in order to minimize background readings, mitochondria may be separated from incubation medium, which prevents continued mitochondrial respiration. Continued respiration generates $H_2O_2$, which reduces sensitivity and/or accuracy.

The medium used for the assay exemplified contains 130 mM KCl, 20 mM Tris-Hepes, 10 µM EGTA, 0.096% ethanol pH 7.5 at about 25° C. Stock solution of $NAD^+$ of 50 µM was prepared in de-ionized water. The assay was carried out in 2 ml volume of the above mentioned medium with 1.5 U/ml of ADH, 50 mU/ml NADH Oxidase, 5 U/ml of HPP, and 20 µM Amplex Red.

FIGS. 2 thru 5 show that the described assay mixture exhibits negligible background fluorescence. Following $NAD^+$ addition at the indicated time points, Resorufin was formed, as detected by an increase in fluorescence intensity. What is more, the assay demonstrates a linear relationship between $NAD^+$ concentration and relative fluorescence and may further be used to detect nanomolar concentrations of pyridine nucleotides. The calibration curves (FIGS. 3 and 4) demonstrate that this assay may be highly sensitive, allowing detection of nanomolar concentration changes in $NAD^+$ levels. Thus, the release of pyridine nucleotides, by even a small fraction of mitochondria, are detected by the methods of the present invention.

Figure 5:
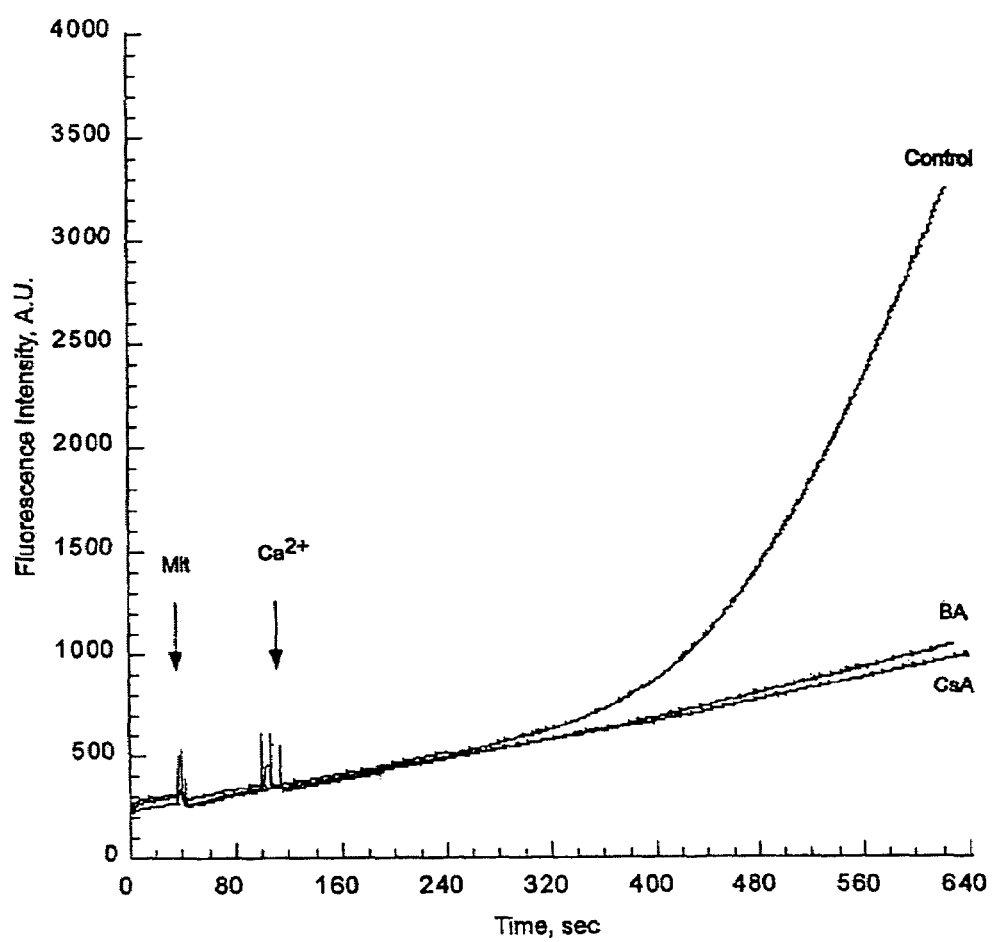
FIG. 5 illustrates the recording of fluorescence intensity following calcium additions to isolated liver mitochondria in the assay mixture. Controls; only calcium (100 µM) was added. BA; the same amount of calcium (100 µM) was added to mitochondria incubated in the presence of 20 µM Bongrekig acid. CsA; mitochondria were incubated in the presence of cyclosporine A (1 µM).

FIG. 5 indicates the addition of calcium to isolated liver mitochondria, and consequently release of PNs, is detected as leads to increased production of Resorufin fluorescence. Calcium is known to induce opening of the MPT pore. The increase in fluorescence following calcium addition could be blocked by MPT inhibitors cyclosporine A (CsA, 1 μM), and Bongkrekic acid (BA, 20 μM) demonstrating the specificity of the assay.

Experiments with isolated liver mitochondria were carried out in the same medium as those without; however, no substrate was added, since respiring mitochondria produce superoxide ($O_2^-$). Superoxide is converted into ($H_2O_2$) by manganese superoxide dismutase (MnSOD). Leakage of $H_2O_2$ into the medium is expected to give a increase in fluorescence intensity which is not due to the release of pyridine nucleotides from mitochondria. However, as demonstrated in FIG. 5, in the absence of substrate the background fluorescence is low indicating that the mitochondria did not release $H_2O_2$. Only following the calcium additions, was a gradual increase in fluorescence intensity observed. This increase was not due to $H_2O_2$ production by mitochondria because calcium addition did not induce Resoflirin generation when only HRP and Amplex red were present in the medium.

Figure 6:
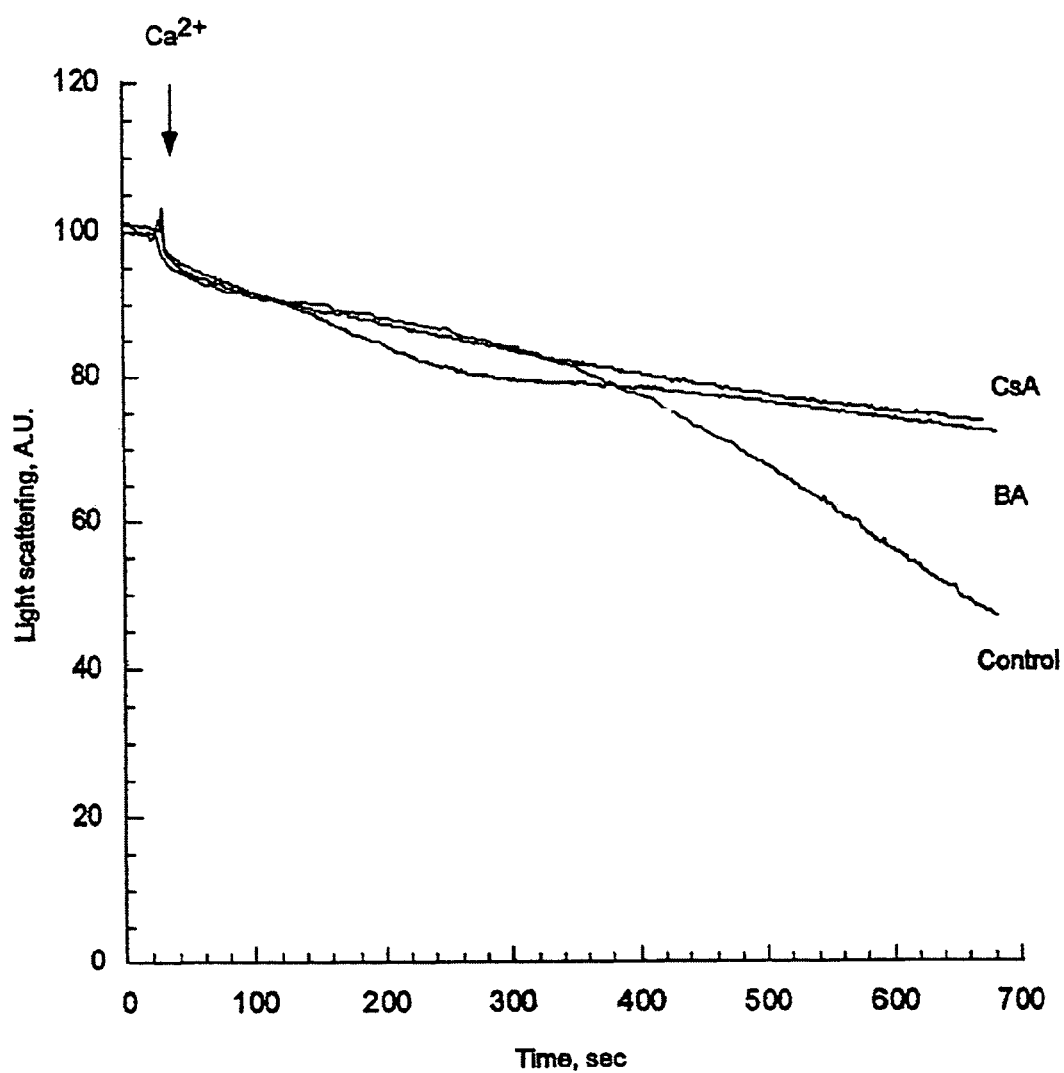
FIG. 6 illustrates calcium-induced swelling of mitochondria isolated from whole liver. The swelling is detected by recording the light scattering of mitochondrial suspension at 540 nm. Experimental conditions are the same as described in FIG. 5, except no enzymes were present in the medium.

The opening of the MPT pore leads to osmotic swelling of mitochondria, which can be detected as decreased light scattering. FIG. 6 shows that there was a slight decrease in the light scattering due to calcium addition, which was not immediately accompanied by $NAD^+$ release from mitochondria. However, a more significant and progressive decrease in light scattering starting at about 300 sec. following the initial calcium pulse occurred. At the same time (i.e., 300 sec.), an increase in Resorufin production (FIG. 5) was observed, indicating that the swelling was likely accompanied by release of pyridine nucleotides from the mitochondria. The swelling was also inhibited both by CsA and BA, suggesting that the pathologic increase in their membrane permeability was due to MPT pore opening.

Because the inventive assays described herein are based on detection of the release of endogenous compounds (e.g., pyridine nucleotides) from mitochondria, loading or manipulation of mitochondria is not required or necessary. Moreover, the methods of the present invention does not require control experiments to exclude possible uncoupling, respiratory inhibition or calcium uptake blocking because under these conditions, the mitochondrial membrane remain intact and the PN are not released.

Male Wistar rats weighing about 300 g were used for isolation of rat liver mitochondria. For examination of calcium-induced release of $NAD^+$, 0.125 mg/ml of mitochondrial protein were used. The mitochondria were incubated in 2 ml of the reaction buffer containing all compounds required for the assay.

Resorufin is a highly fluorescent compound well-known in the art, which can be detected by excitation at 550 nm and emission at 585 mn. Fluorescence of may be measured by employing any fluorescence spectrometer, such as, for example, the Hitachi 2500 (Tokyo, Japan). The production of a detectable signal may be adapted for real-time or near-real-time monitoring through multiple readings over incrementally shorter time-spans.

Apart from isolated mitochondria, the assays described herein may also be adapted for whole cell applications. In embodiments where the intra-mitochondrial solute is a PN, their presence in the cytoplasm itself may generate a background signal, even in the absence of damage to mitochondria. In such an event, it may be necessary to first deplete the cells of cytosolic PNs. In one approach, this may be performed by permeabilization of cell membranes to leak the intracellular solutes from the cells into an incubation media. After the cytosolic solutes have sufficiently diffused from the cells, the medium may be removed, or the cells washed, and replaced with new medium containing an assay mixture. This permeabilization procedure may allow assay components to pass into the cells and detect damage to mitochondria when present.

A variety of primary cells and cell lines may be used in the instant invention. In some embodiments, neuronal and astrocytic cell cultures and also several cell lines (e.g., PC 12 cells, SY5Y cells, C6 glioma cells) may be desirable. Cell permeabilization techniques are well known in the art, all of which may be employed herein. For example, digitonin (about 10 μM to about 30 μM, depending on cell density) permeabilizes cell membranes for solutes since digitonin binds and remove cholesterol leaving holes in the cell membranes. Saponins may also be used as permeabilization agents.

It will be apparent to one of ordinary skill in the art from the teachings disclosed herein, the many applications of the instant invention. Such embodiments explicitly fall within the scope of the present invention. Non-limiting examples will now be described.

The enzymatic assays of the present invention may be suitable for screening of compounds that protect mitochondria against membrane damage. In one instance, experimental conditions may be derived to model pathological damage to mitochondrial membranes. As noted above, calcium may be used, but the scope of mitochondrial damaging agents is, by no means, limited thereto. Nonetheless, once conditions for inducing membrane permeation are determined, one to an unlimited number of compounds may be rapidly screened for their respective ability to retard and/or prevent the induced permeability. Non-limiting examples of such compounds include CsA and BA. CsA, in particular, inhibits MPT and can dramatically ameliorate brain damage due to ischemic insult. Furthermore, CsA also has a protective effect in brain damage induced by hypoglycemic coma, focal ischemia, and trauma.

Alternatively, the assays of the present invention may be tailored for screening of compounds that damage or otherwise perturb the integrity of mitochondrial membranes. For example, isolated mitochondria or mitochondria from whole cells may be subjected to a panel of test compounds—in the presence of enzymatic assays of the instant invention—to determine which, if any, of the compounds produces a detectable signal, indicating membrane damage. The intensity of the signal and the rate at which the signal is generated may also be correlated with the efficacy of the compound in compromising membrane integrity. Compounds that have such activity may have therapeutic applications, in which cell-death is warranted and/or desired, such as, for example, therapeutic compounds used in cancer treatment.

In one embodiment, 96-well plates may be prepared with pre-determined amounts of mitochondria, compound of interest, and enzymes of the instant invention. Membrane damaging agents may then be introduced to some or each of the wells, whereupon the rate and magnitude of membrane permeability to intra-mitochondrial membranes may be assessed in a spectrophotometer or luminometer. In this way, compounds from wells exhibiting reduced membrane permeability, as compared with controls, may be selected for further study. In a similar manner, the instant invention may also be tailored to study and screen for compounds that adversely affect the permeability of mitochondrial membranes.

The enzymatic methods described herein for measuring concentrations of intra-mitochondrial compounds in biological samples of isolated mitochondrial may also be performed, for example, by using pre-packaged diagnostic kits. Such kits optionally include components such as ADH, NADH Ox, HRP, and enzyme reagents for carrying out the steps of the methods of the invention (e.g., Amplex Red or other reagent for signal detection). Also optionally included are ancillary agents such as buffering agents, substrate reagents such as ethanol, and agents to aid transport or storage of the samples.

Kits embodying the enzymatic method aspect of the invention may also include control standards such as NADH, $H_2O_2$, Amplex red, HRP, and Resorufin in defined concentrations. The kits may also include an apparatus or container for conducting the methods of the invention and/or transferring samples to a diagnostic laboratory for processing, as well as suitable instructions for carrying out the methods of the invention. If the kit is to be used in a disease detection method of the invention, the kit may also optionally include components for the detection of other disease markers.

The methods of the invention can be used to provide a relatively rapid and economical screen of large numbers of patients to promote early diagnosis of disease(s) associated with altered levels of mitochondrial membrane permeability. The methods disclosed herein are simple, marginally invasive, and require only a specimen from the patient. Early detection provided by such methods may significantly improve quality of life and better patient survival rates by permitting the early and aggressive management of the disease at nascent stages. Thus, such methods are also useful for screening patients who have not been previously diagnosed with a disease, particularly patients who are at high risk for developing the disease.

In preferred methods of the disease detection aspect of the invention, the mitochondrial membrane permeability level of the patient is determined or monitored utilizing the enzymatic detection aspect of the invention described above. The specific correlation of the level of mitochondrial membrane permeability in the sample with the disease state is expected to be specific for the type of disease. A person of ordinary skill in the art would be capable of determining the proper level of mitochondrial membrane permeability in the sample which is indicative of a particular disease state utilizing routine experimentation.

For instance, one of ordinary skill in the art would know to first establish a positive indicator threshold level of mitochondrial membrane permeability for a particular sample by first comparing samples taken from normal patients with those diagnosed as having the particular disease. Alternatively, normal or control values may be obtained, when known, from published literature. By making a comparison between normal or control values and those indicative of disease, utilizing samples available from various specimen banks and the assay techniques detailed below, one may establish the proper indicative threshold to diagnose a patient as having a particular disease.

In addition to its use as a detection method, the response of a disease condition to treatment may be monitored using the methods of the present invention by determining mitochondrial membrane permeability in samples taken from a patient over time. The mitochondrial membrane permeability may be measured and compared that taken at the earlier time from that patient. If there is a significant change in mitochondrial membrane permeability over time, it may indicate an increase in the severity of the condition in the patient. Conversely, if there is a normalization, it may indicate an improvement in the condition of the patient. Samples suitable for the present invention include, but are not limited to, blood, tissue, a body fluid such as, for example, serum, plasma, urine, sweat and saliva. In certain embodiments, the sample comprises hepatic (liver) tissue.

Without being limited to or bound by theory, it is believed that mitochondrial damage in some cases may be due to calcium overload an/or oxidative stress. In any event, it follows that therapeutic protection of mitochondrial integrity and function may provide treatment or prevention disease. Examples of injury or disease, which may cause damage to mitochondrial membranes include, for example, ischemia, hypoxia, anoxia, hypoglycemic coma, seizures, stroke, physical trauma, myocardial infarction, drug or chemical toxicity, Alzheimer's disease, Parkinson's disease, Huntington disease. Accordingly, the use of the assay to discover new pharmaceutical agents may have potential therapeutic effects against at least one, some, or all of the aforementioned diseases.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

What is claimed:

1. A method of assessing the integrity of a mitochondrial membrane, comprising:
   (a) contacting a sample comprising isolated mitochondria with a mixture of enzymes comprising alcohol dehydrogenase (ADH), NADH oxidase (Ox), and horseradish peroxidase (HRP), which mixture catalyzes at least two coupled, cyclic enzymatic reactions that utilize an intra-mitochondrial substance, if present in the sample, as a substrate in at least one of said coupled, cyclic enzymatic reactions and in which at least the other of said coupled, cyclic enzymatic reactions generates a detectable signal; and
   (b) correlating said detectable signal, if generated, to the presence of said intra-mitochondrial substance, thereby implicating a breach in said mitochondrial membrane.

2. The method of claim 1 in which the intra-mitochondrial substance is a pyridine nucleotide.

3. The method of claim 2 in which the pyridine nucleotide is $NAD^+$ or NADH.

4. The method of claim 1 in which the isolated mitochondria are isolated from liver.

5. The method of claim 1 in which the detectable signal is a luminescent product, a fluorescent product, or a spectrophotometrically detectable product.

6. The method of claim 1, wherein, prior to step (a), said sample is contacted with one or more test compounds; and then the detectable signal produced in the presence of the test compound is compared to the detectable signal produced in the absence of the test compound to determine the effect of the test compound on the integrity of the mitochondrial membrane.

7. The method of claim 6, wherein the test agent is a mitochondrial membrane damaging agent.

8. The method of claim 7, wherein said mitochondria damaging agent is cyclosporin A, calcium, or Bongkrekic acid.

* * * * *